(12) United States Patent
Gerhardt et al.

(10) Patent No.: US 9,829,470 B2
(45) Date of Patent: Nov. 28, 2017

(54) SYSTEMS AND METHODS OF COMPENSATION FOR CHROMATOGRAPHY COLUMN VOLUME VARIATIONS

(71) Applicant: Waters Technologies Corporation, Milford, MA (US)

(72) Inventors: Geoff C. Gerhardt, Woonsocket, RI (US); Martin Gilar, Franklin, MA (US); Bernard Bunner, Newton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 16 days.

(21) Appl. No.: 14/898,272

(22) PCT Filed: Jun. 17, 2014

(86) PCT No.: PCT/US2014/042626
§ 371 (c)(1),
(2) Date: Dec. 14, 2015

(87) PCT Pub. No.: WO2014/204893
PCT Pub. Date: Dec. 24, 2014

(65) Prior Publication Data
US 2016/0139095 A1  May 19, 2016

Related U.S. Application Data

(60) Provisional application No. 61/835,763, filed on Jun. 17, 2013.

(51) Int. Cl.
*G01N 30/20* (2006.01)
*G01N 30/86* (2006.01)
(Continued)

(52) U.S. Cl.
CPC ..... *G01N 30/8668* (2013.01); *G01N 30/8665* (2013.01); *G01N 30/6095* (2013.01); *G01N 2030/027* (2013.01)

(58) Field of Classification Search
CPC ..................................................... G01N 30/20
See application file for complete search history.

(56) References Cited

U.S. PATENT DOCUMENTS

| 3,926,800 A | 12/1975 | Stephens |
| 4,003,243 A | 1/1977 | Blu et al. |

(Continued)

FOREIGN PATENT DOCUMENTS

| EP | 0218163 A2 | 4/1987 |
| WO | 2009094331 A1 | 7/2009 |

OTHER PUBLICATIONS

International Preliminary Report on Patentability in counterpart PCT/US14/42626, dated Dec. 30, 2015; 8 pages.

(Continued)

*Primary Examiner* — Robert R Raevis
(74) *Attorney, Agent, or Firm* — Schmeiser, Olsen & Watts LLP

(57) ABSTRACT

Provided are systems and methods for adapting to volume variations in microfluidic chromatography columns. A column is calibrated by comparing a parameter of the column with a same parameter of a reference column and generating, by a processor, an adjustment factor in response to the comparison between the parameter of the column with a same parameter of the reference column. Volume differences between the calibrated column and the reference column are compensated for by integrating the generated adjustment factor into a sample separation involving the calibrated column.

17 Claims, 7 Drawing Sheets

(51) Int. Cl.
    *G01N 30/60*         (2006.01)
    *G01N 30/02*         (2006.01)

(56)                   References Cited

U.S. PATENT DOCUMENTS

| | | |
|---|---|---|
| 6,691,053 B2 | 2/2004 | Quimby et al. |
| 6,712,085 B2 | 3/2004 | Weissgerber et al. |
| 7,178,386 B1 | 2/2007 | Gamble et al. |
| 2008/0003572 A1 | 1/2008 | Delamarche et al. |
| 2010/0101411 A1 | 4/2010 | Tipler |
| 2011/0104826 A1 | 5/2011 | Gibbons et al. |
| 2011/0260051 A1 | 10/2011 | Preudhomme et al. |

OTHER PUBLICATIONS

International Search Report & Written Opinion in counterpart international patent application No. PCT/US14/42626, dated Nov. 25, 2014; 11 pages.
Extended European Search Report in counterpart European Patent Application No. 14814033.8, dated Mar. 7, 2017; 8 pages.

SYSTEMS AND METHODS OF COMPENSATION FOR CHROMATOGRAPHY COLUMN VOLUME VARIATIONS

RELATED APPLICATIONS

This application claims the benefit of and priority to U.S. provisional application No. 61/835,763, filed Jun. 17, 2013, entitled "Systems and Methods of Compensation for Chromatography Column Variations", the entirety of which is incorporated by reference herein.

FIELD OF THE INVENTION

The present invention relates generally to the field of chromatography, and more specifically, to systems and methods that compensate for variations in microfluidic liquid chromatography (LC) column volumes.

BACKGROUND

Conventional microfluidic LC columns are manufactured to fine tolerances in an attempt to effect reproducible separations of compounds or the like, especially closely related compounds. Since microfluidic LC columns are formed having very small dimensions, for example, inner diameters ranging from 75 to 500 microns, columns intended to have the same volume may nevertheless exhibit a degree of variability with respect to each other. For example, two columns may each be configured to have a volume of 0.3 mm. However, machining errors can result in a column volume difference between these two columns, which can impact the reproducibility of chromatographic results.

BRIEF SUMMARY

In accordance with one aspect, provided is a method for adapting to volume variations in microfluidic chromatography columns. The method comprises calibrating a column by comparing a parameter of the column with a same parameter of a reference column; and generating, by a processor, an adjustment factor in response to the comparison between the parameter of the column and the same parameter of the reference column. The method further comprises compensating for volume differences between the calibrated column and the reference column by integrating the generated adjustment factor into a sample separation involving the calibrated column.

In accordance with one aspect, provided is a column volume compensation system, comprising: a column volume comparator that compares a parameter of a column with a same parameter of a reference column; an adjustment factor processor that generates an adjustment factor in response to the comparison between the parameter of the column and the same parameter of the reference column; and an adjustment module that compensates for volume differences between the column and the reference column by integrating the generated adjustment factor into a sample separation involving the column.

In accordance with an aspect, provided is a method for compensating for volume variations in a microfluidic chromatography device. The method comprises comparing a parameter of a column and the same parameter of a reference column generating, by a processor, an adjustment factor in response to the comparison between the parameter of the column with a same parameter of the reference column; performing a sample separation with the column; and adjusting a flow rate of the sample separation according to the adjustment factor.

In accordance with another aspect, provided is a method for compensating for chromatography column volume variations, comprising: injecting a first tracer compound into a chromatography system without an installed column; measuring a first tracer passage time at the chromatography system without an installed column; determining a first volume of the chromatography system without an installed column from a retention time of the chromatography system without an installed column; injecting a second tracer compound into the chromatography system including a column; measuring a second tracer passage time at the chromatography system including the column; determining a second volume of the chromatography system including the column from the system retention time; determining a net volume from the first volume and the second volume; and generating a flow rate adjustment factor from the net volume and a reference volume.

BRIEF DESCRIPTION

The above and further advantages of embodiments of the present inventive concepts may be better understood by referring to the following description in conjunction with the accompanying drawings, in which like numerals indicate like structural elements and features in various figures. The drawings are not necessarily to scale, emphasis instead being placed upon illustrating the principles of the invention.

Figure 6:
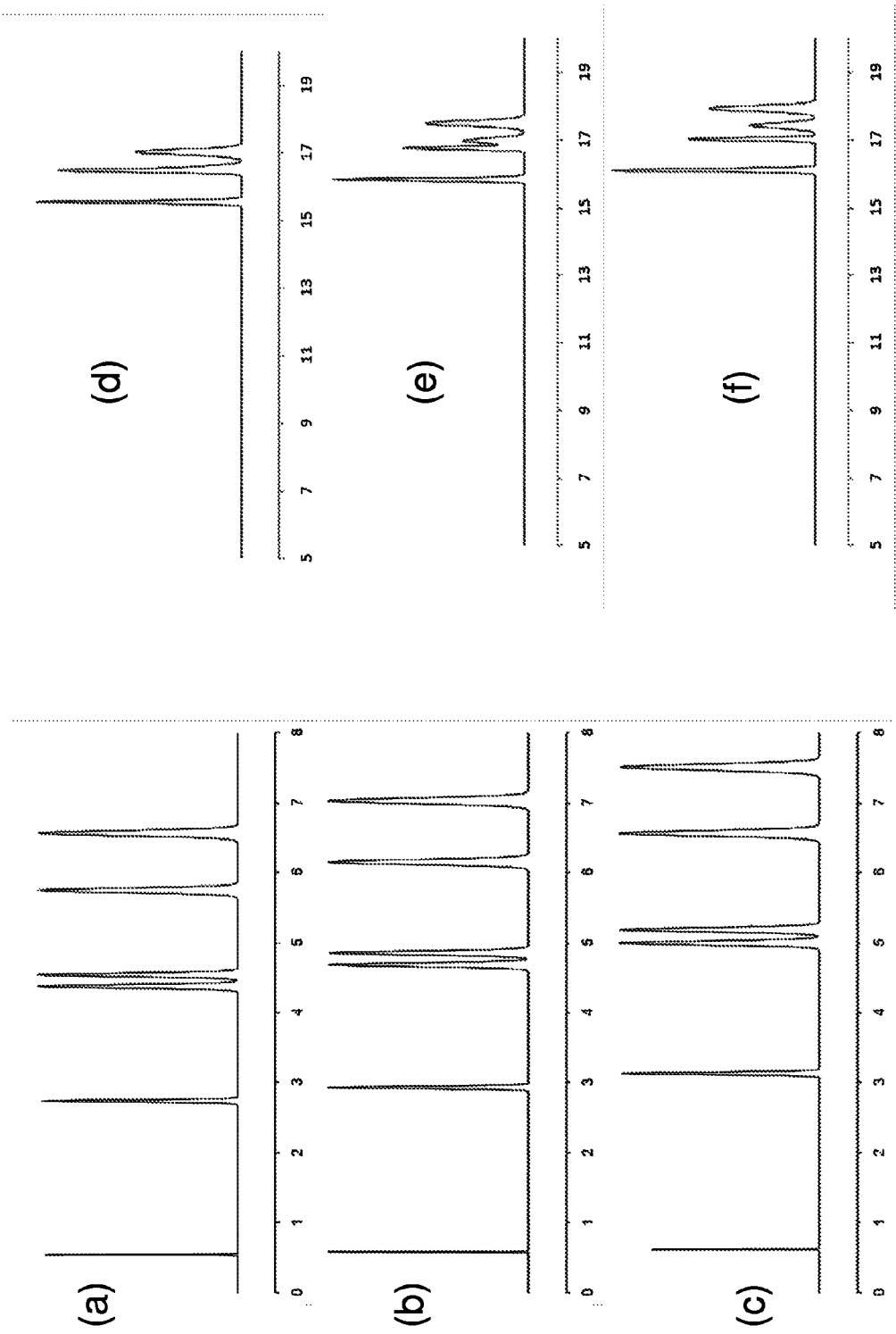
Figure 7:
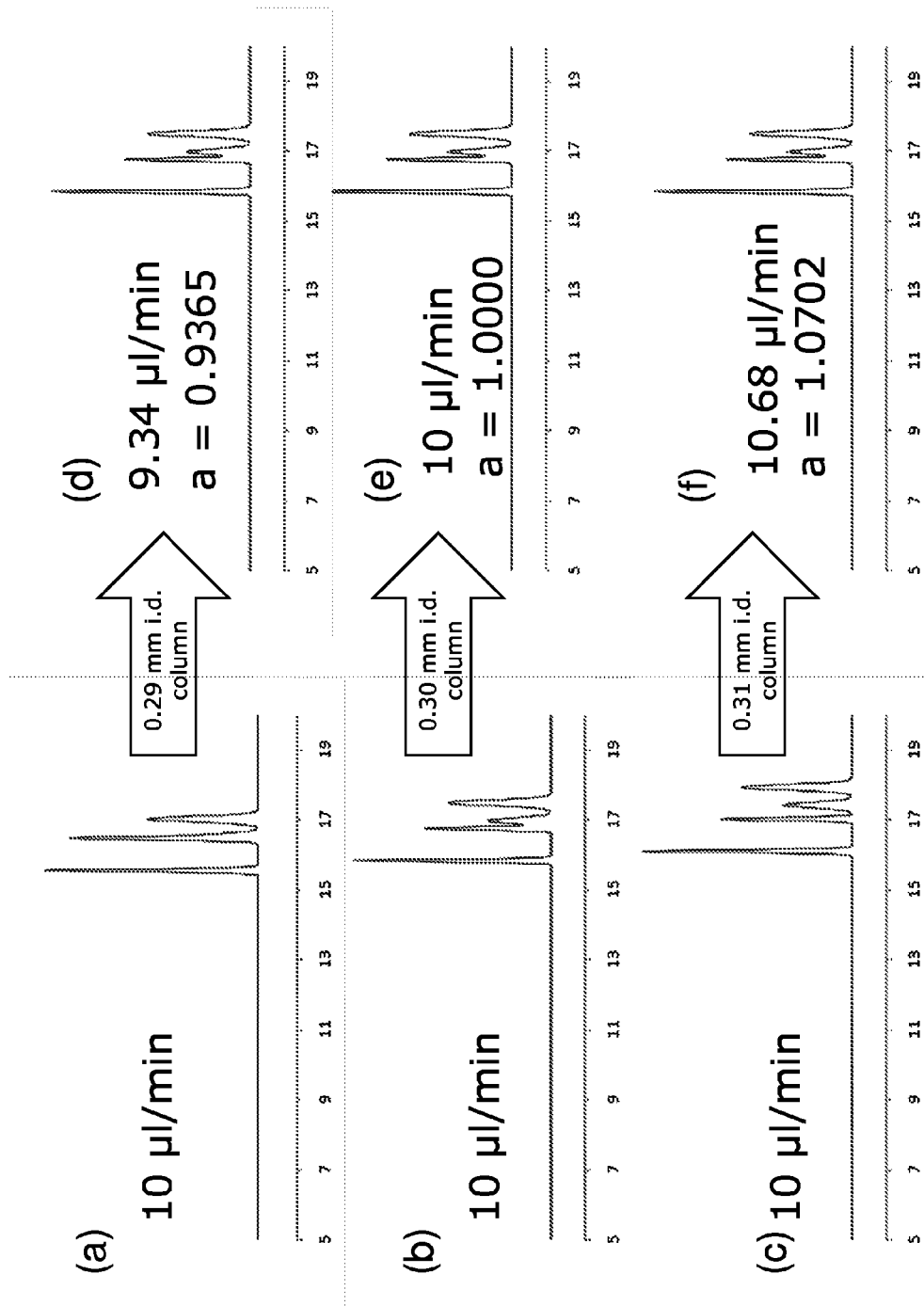

FIGS. 6(a)-6(c) are graphs illustrating the effects of column inner diameter variations on isocratic mode results;

FIGS. 6(d)-6(f) are graphs illustrating the effects of column inner diameter variations on gradient mode results;

FIGS. 7(a)-7(c) are graphs illustrating the effects of column inner diameter variations on gradient mode results; and FIGS. 7(d)-7(f) are graphs illustrating the results of compensating for column inner diameter variations, in accordance with an embodiment.

DETAILED DESCRIPTION

Reference in the specification to "one embodiment" or "an embodiment" means that a particular, feature, structure or characteristic described in connection with the embodiment is included in at least one embodiment of the teaching.

References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

FIG. 1A is an exploded view of a microfluidic column device 100, in which embodiments of the present inventive concepts can be practiced. FIG. 1B is an assembled perspective view of the microfluidic column device 100 of FIG. 1A. FIG. 1C is a cross-sectional view of the microfluidic column device 100 of FIGS. 1A and 1B.

The microfluidic column device 100 can include a chromatography capillary column, for example, a high-performance liquid chromatography (HPLC) or other analytical column that interfaces between an injector or the like and a detector and/or analyzer such as an electrospray mass spectrometry unit. Accordingly, the microfluidic column device 100 can be constructed and arranged for chromatography-related applications. A stationary phase or related medium can be positioned in the microfluidic column device 100 for separating components in a sample transferred with a mobile phase through the device 100.

In an embodiment, the microfluidic column device 100 is formed of a plurality of flat substrates 102, 104, 106, which can be in the form of wafers or the like. The substrates 102, 104, 106 can be formed of, but not limited to, ceramic, silicon, glass, polymers, and/or metals such as titanium. Thus, the microfluidic column device 100 can be constructed and arranged as a planar chip-based separation device, but is not limited thereto. For example, the microfluidic column device 100 can be tubular, polygon-shaped, or be of another shape, size, or configuration that is well-known to those of ordinary skill in the art.

The center substrate 106 can be etched, for example, machined, electrochemically etched, or the like, to form one or more separation channels 108, for example, which extend through at least a portion of a surface of the center substrate 106. The separation channel 108 can have a cross-sectional profile that is rectangular, for example, as shown in FIG. 1C, or polygonal, elliptical, semi-elliptical, or have another shape, size, and/or other configuration parameter known to those of ordinary skill in the art. The other substrates 102, 104 can be formed to include one or more channels, similar to the separation channel 108 formed in the substrate 106. For example, one or more separation channels can be formed in the substrate 102, in addition to or instead of the center substrate 106. Other column channels can be formed in the substrates, including but not limited to flow channels, injection channels, eluent reservoirs, inlets, outlets, vias, or a combination thereof.

The substrates 102, 104, 106 are coupled to each other such that the center substrate 106, and thus the separation channel 108, is sandwiched between two or more other substrates 102, 104. The substrates 102, 104, 106 can be coupled together by bonding, adhesives, or other coupling technique known to those of ordinary skill in the art.

Although not shown, the microfluidic column device 100 can integrate some or all of the necessary components, for example, resident on or between the substrates 102, 104, 106, for performing a standalone chromatography operation, including but not limited to miniaturized pumps, valves, electrical contacts, flow sensors, autosamplers, electrospray tips, guard columns, sample trap columns, two-dimensional chromatography elements, or a combination thereof. Alternatively, one or more of these elements can be external to the microfluidic column 100, for example, resident at the delivery system 202 shown in FIG. 2.

A first hole 110A can be formed through the substrate 102 on one side of the center substrate 106 and/or other intervening wafers or the like between substrates 102 and 106, to intersect one end of the separation channel 108. Similarly, a second hole 110B can be formed through at least one substrate 102, and/or other intervening wafers or the like between substrates 102 and 106, to intersect another end of the separation channel 108. Accordingly, a fluid path can be formed from the first hole 110A to the second hole 110B via the separation channel 108. The holes 110A, 110B (generally, 110) can be used as inlets, outlets, injection channels, mass spectrometer inlets, vias, and so on, for example, for receiving and/or outputting a fluid from adjacent devices. In other embodiments, one or more holes can be at an edge of a substrate and extend along at least a portion of a length or width of a substrate 102, 104, and/or 106, for example, in a horizontal direction. Here, the holes can be provided in addition to or alternatively to the holes 110 extending through at least a portion of the substrate 102, 104, and/or 106.

The small dimensions of the microfluidic column device 100, for example, an inner diameter ranging from 75 to 500 microns, can result in fabrication errors causing misalignments, for example, shown in FIG. 1C at a region A, where a hole 110 is not precisely aligned with the end of the separation channel 108. Although machining tolerances may be anticipated in manufacturing environments where a plurality of devices 100 are formed due to the narrow microscale specifications, misalignments or other machining errors can nevertheless occur. For example, a machining variability of a few micrometers may result in a large device volume variation, or related variations such as inner diameter variations. Since retention times are proportional to column volumes, column volume variations can result in an unacceptable variability in an achieved chromatographic separation. For example, a microfluidic column manufactured according to a square profile, e.g., 85×85 μm, and having a machining error of 2 μm, i.e., 87×87 μm, may have a 5% greater column volume. A machining error of 10 μm, i.e., 95×95 μm, can result in a 25% greater column volume. The effects of varying column volumes on chromatography are illustrated by way of example at FIGS. 6(a)-6(f).

While accurate and consistent retention time measurements are imperative with respect to isocratic elution, retention variations may be less important when gradient elution is used as a chromatographic separation mode. Nevertheless, column volume discrepancies can alter the apparent gradient slope (s), for example, as shown in equation 1 (Eq. 1):

$$s = \Delta C \cdot (t_0/t_g) = \Delta C \cdot (V_0/V_g) \tag{Eq. 1}$$

In Eq. 1, $\Delta C$ is a gradient range, for example, 0-50% of acetonitrile corresponds to $\Delta c=0.5$), $t_0$ is a void time measured as the elution time of an unretained component, $t_g$ is a time of the gradient, and $V_0$ and $V_g$ are the gradient volume and gradient void volume, respectively. Accordingly, if the volume of the microfluidic column increases, $V_0$ also increases. However, since the gradient time, e.g., $t_g$, remains constant, the gradient slope (s) increases. The slope (s) can affect the gradient separation selectivity. Thus, a machining error, which can result in a variability in column volume, can alter chromatography results, for example, with respect to a relative peak elution. This effect can be detrimental in applications such as peptide mapping or any separation of complex samples with peaks closely adjacent each other, i.e., critical pairs.

In brief overview, embodiments of the present inventive concepts relate to a system and method that adjusts the flow rate at which a separation is performed in a microfluidic chromatography column, which can compensate for the undesirable variability between different column volumes and overcome the issues related to retention time in an isocratic mode and/or separation selectivity in a gradient mode.

Figure 1:
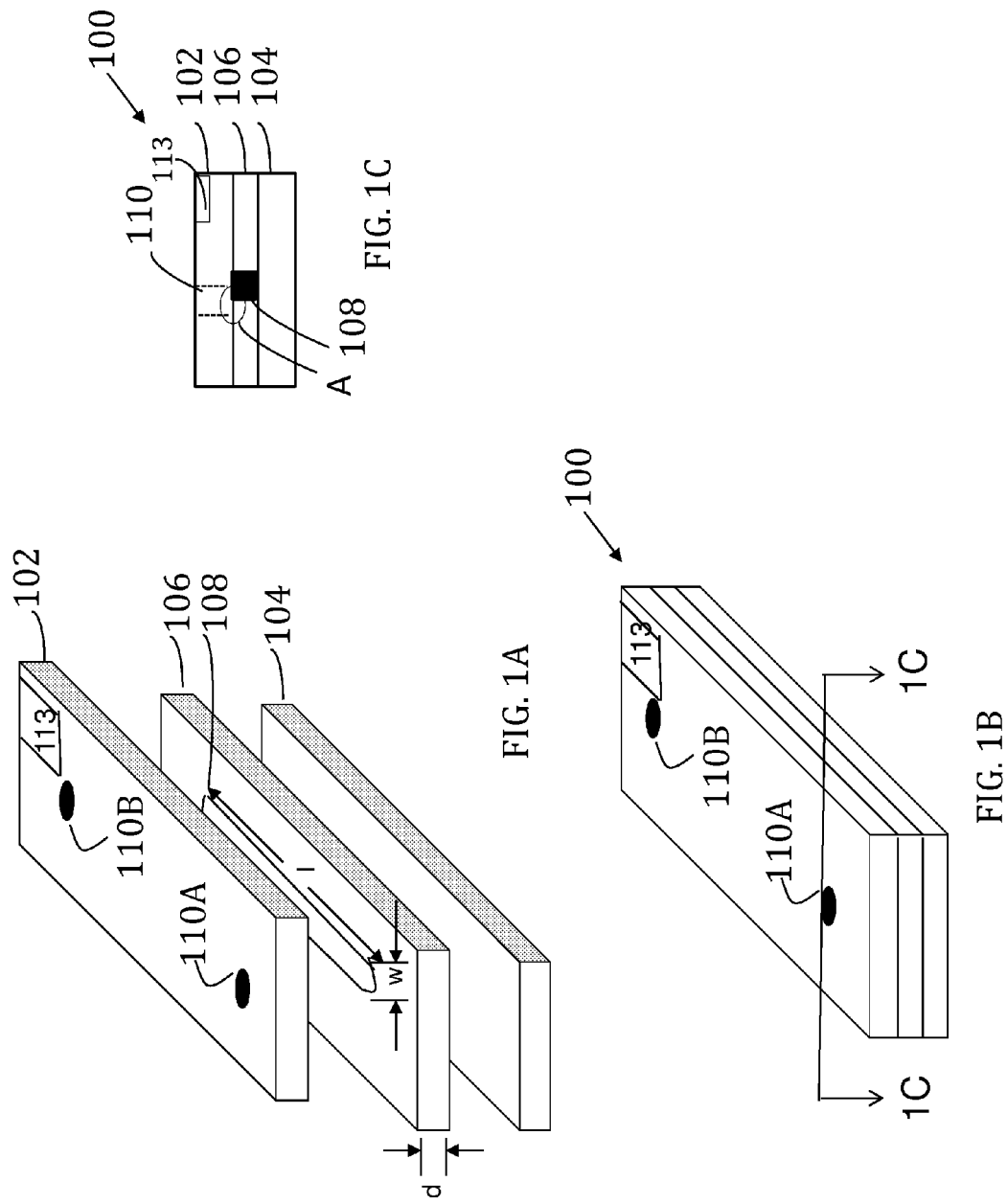
FIG. 1A is an exploded view of a chromatography column, in which embodiments of the present inventive concepts can be practiced.
FIG. 1B is an assembled perspective view of the chromatography column of FIG. 1A.
FIG. 1C is a cross-sectional view of the chromatography column of FIGS. 1A and 1B, illustrating a volume variation.

During operation, a chromatography system is provided with a microfluidic column device having a predetermined volume, for example, a known or measured volume of the separation channel 108 of FIG. 1 between an injector/delivery system and a detector/analyzer. The column device need only be calibrated once. Calibration can occur in a factory as part of testing of the column device, e.g., a chip. Alternatively, calibration can occur as part of a system quality control process, at a customer site, a quality assurance facility, or other location.

Information related to the column device volume can be compared to a "reference" device as part of a calibration, for example, a reference column device, or standard column device, having similar, and known, parameters and/or characteristics, for example, a known column volume, inner diameter, and/or other dimensions. For example, a column volume can be determined according to a formula well-known to those of ordinary skill in the art. For example, a rectangular reference column volume can be determined from a length (l), width (w), and height or depth (d) of the channel 108. In another example, a cylindrical shaped volume of the channel 108 can be determined from the diameter and length of the channel 108. In other embodiments, a reference column is not required so long as the actual test flow rate and system volume are known.

In an embodiment, a column volume compensation system generates a flow rate adjustment factor based on a comparison result between a known parameter of a reference column and that of a column for performing a calibration, such as volume and/or retention time. The flow rate adjustment factor can be a ratio of the column volume and the reference column volume, or a ratio of the column retention time and the reference column retention time. The flow rate adjustment factor can be applied to flow rate calculations performed with respect to samples applied to the column after calibration. Accordingly, the flow rate can be adjusted according to the flow rate adjustment factor to compensate for volume differences between the column device after calibration and the reference column.

The flow rate adjustment factor can be applied during subsequent operations of the column device after calibration, for example, applied to each newly manufactured column. For example, inventive concepts can be applied to the same column that has been calibrated, that is, an adjustment factor can be determined from the column and subsequent measurements can be performed using this same column that has been calibrated. A flow rate adjustment factor can be obtained for each column by performing a calibration in accordance with an embodiment, for example, described herein, and applied for subsequent operations of the column. Accordingly, an operator can select a desirable nominal flow rate during a sample analysis, whereby a corrected flow rate is automatically applied for the analysis. Thus, a user-determined or nominal flow rate for a particular column device may be adjusted. Therefore, reproducible column performance can be obtained regardless of column-to-column volume variability. By adjusting the flow rate in this manner to compensate for device volume deviations, the same retention time between different columns can be maintained. Also, or alternatively, the same gradient slope can be maintained, thereby assuring a reproducible separation selectivity of a gradient chromatography analysis.

Figure 2:
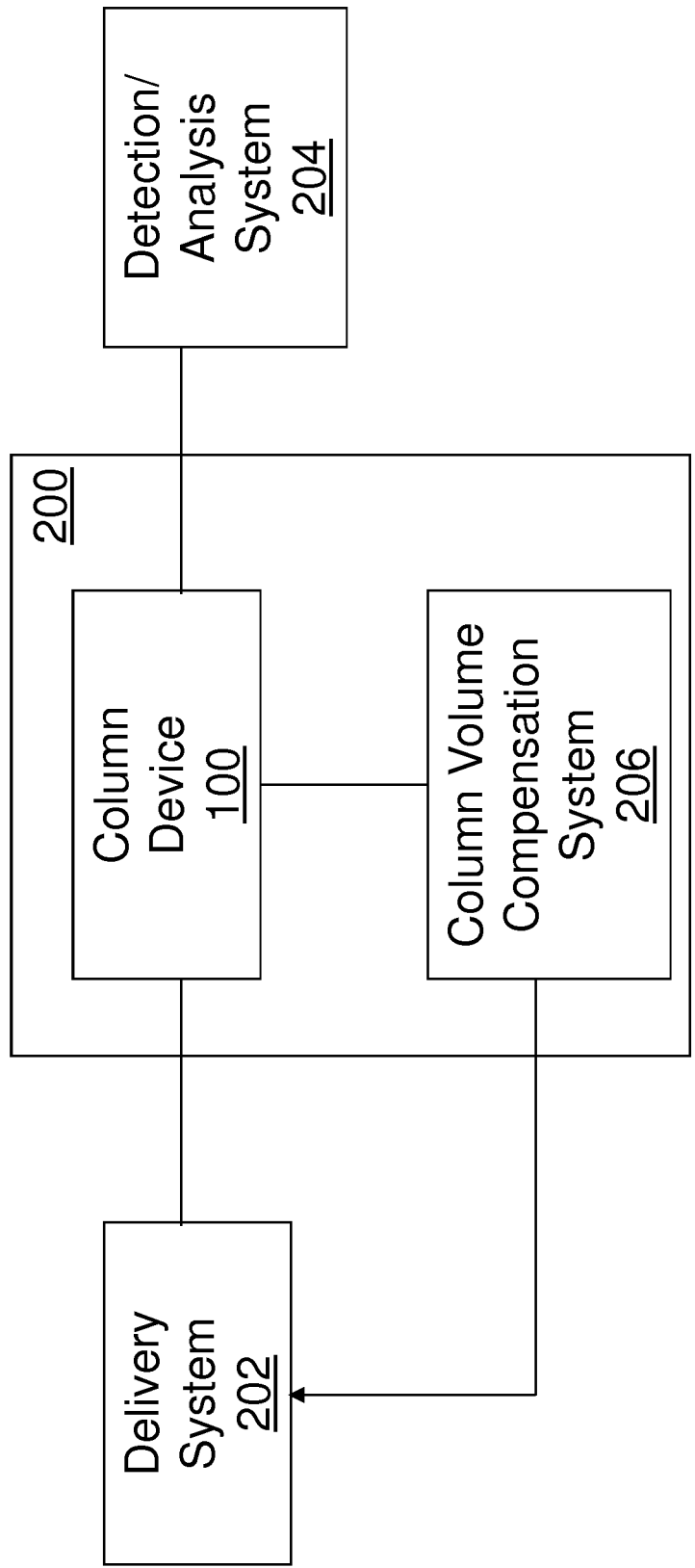
FIG. 2 is a schematic view of a chromatography system, in accordance with an embodiment.

FIG. 2 is a schematic view of a chromatography system 200, in accordance with an embodiment. The microfluidic column device 100 of FIGS. 1A-1D can be inserted in a microfluidic chromatography system 200, which can serve as an interface between a delivery system 202 and an analysis system 204. The system 200 compensates for volume variations among different microfluidic columns in accordance with an embodiment.

The delivery system 202 can deliver to the column 100 a mobile phase of constant composition, i.e., isocratic elution, or varying composition, i.e., gradient elution. The delivery system 202 can include an injector, pre-column, pump, valves, and/or other elements for delivering a sample to the microfluidic chromatography system 200. The microfluidic chromatography system 200 can include a spray tip (not shown) or the like which outputs the sample to a detection/analysis system 204, which can include a detector and/or analyzer such as an electrospray mass spectrometry unit. Although the microfluidic chromatography system 200 is illustrated in FIG. 2 as being separate from the delivery system 202 and the detection/analysis system 204, in other embodiments, the microfluidic chromatography system 200 is integral with the delivery system 202 and/or the detection/analysis system 204. The chromatography system 200 can have a tubular or planar chip-based configuration, or another shape, size, or configuration that is well-known to those of ordinary skill in the art.

The chromatography system 200 includes a column volume compensation system 206, which can calibrate the column device 100 and/or one or more other separation columns to compensate for volume discrepancies, and can generate a flow rate adjustment factor for use in adjusting a mobile phase flow rate through the calibrated column device 100.

Figure 3:
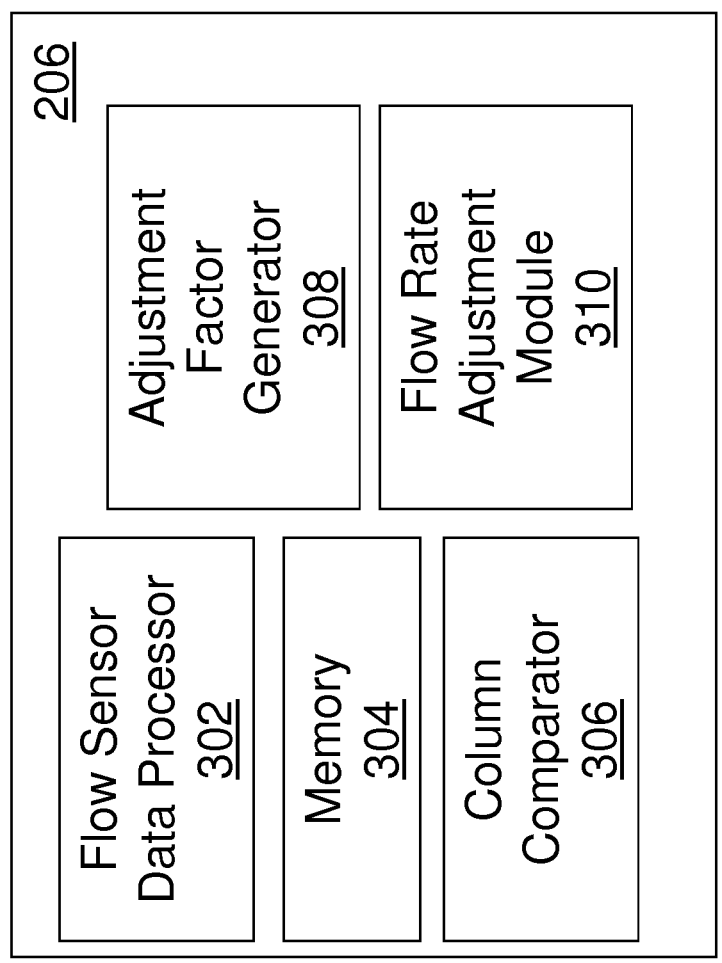
FIG. 3 is a block diagram of the column volume compensation system of FIG. 2, in accordance with an embodiment.

FIG. 3 is a block diagram of the column volume compensation system 206 of FIG. 2, in accordance with an embodiment.

The column volume compensation system 206 can include a flow sensor data processor 302, a memory 304, a column comparator 306, an adjustment factor processor 308, and/or a flow rate adjustment module 310.

The flow sensor data processor 302 can receive data from one or more flow sensors (not shown) at or in communication with the column device 100, which measure and control mobile phase flow rates through the column device 100. The flow rate data can be used for calibrating the column device 100 in accordance with embodiments of the inventive concepts.

The memory 304 can be a non-volatile or volatile memory, for example, DRAM or static RAM (SRAM). Stored at the memory 304 includes program code of an operating system, one or more applications, and/or other software programs executed by a processor. In an embodiment, the memory 304 stores program code that performs one or more methods related to the present inventive concepts, for example, method 400. The memory 304 can store one or more flow rate adjustment factors generated in accordance with embodiments of the present inventive concepts.

The column comparator 306 compares column parameters related to the microfluidic column device 100 with that of a reference column. For example, prior to providing the column device 100 for sample analysis, a reference column can be inserted at the chromatography system 200, and measurements can be taken, such as a retention time of a component through the reference column. Alternatively, reference values can be calculated and/or estimated instead of taking physical measurements of a reference column. Here, a reference column is referred to as a virtual reference column since calculations/estimates are taken in lieu of a physical reference column. In this manner, column and/or system measurements can be determined, for example, a system volume, which includes system-related connectors such as capillaries as well as the column volume. The measurements can be established at the factory, a quality control laboratory, and so on. Other measurements can include flow rate and/or retention time. The reference column known volume and/or other parameter can be compared to a corresponding parameter of the microfluidic column device 100, or other column provided at the chromatography system 200.

The adjustment factor processor 308 generates a flow rate adjustment factor in response to a parameter comparison generated by the column comparator 306. For example, a flow rate adjustment factor can be calculated by dividing a volume of the microfluidic column device 100 by a volume of the reference column. In another example, a flow rate adjustment factor can be calculated by dividing a determined retention time of the microfluidic column device 100 by a determined retention time of the reference column. The column can be empty or at least partially packed, for example, with a stationary phase. The flow rate adjustment factor can be used to adjust a flow rate to match a standard retention time when a flow sensor indicates to the flow sensor data processor that a retention time is longer or shorter than the expected, or standard, retention time.

A well-known chromatographic concept is that a flow rate is proportional to column volume. More specifically, shown in equations (Eqs.) 2A-2C:

$$V = FR^* t,\quad (\text{Eq. 2A})$$

where FR is the flow rate and t is a retention time of a marker.

$$V_R = FR^* t_R,\quad (\text{Eq. 2B})$$

where FR is the flow rate and $t_R$ is a retention time of a marker corresponding to a packed column.

$$V_0 = FR^* t_0,\quad (\text{Eq. 2C})$$

where $V_0$ is a gradient void volume, FR is the flow rate, and $t_0$ is a retention time of an unretained component.

In one embodiment, the flow rate adjustment factor (a) is determined according to the following equation:

$$a = V/Vr,\quad (\text{Eq. 3})$$

where V is the measured volume of the column device 100 and Vr is the reference column volume.

In another embodiment, the flow rate adjustment factor (a) is determined according to the following equation:

$$a = t/t_r,\quad (\text{Eq. 4})$$

where t is the measured retention time of the column device 100 and $t_r$ is the retention time of the column volume.

In an embodiment, column volume compensation can be performed according to equation 5 (Eq. 5):

$$FR(\text{new}) = FR_{(RefNominal)} * a,\quad (\text{Eq. 5})$$

where FR is the adjusted flow rate, a is the flow rate adjustment factor, and $FR_{(RefNominal)}$ is the rate used when performing a calibration, in particular, a preferable flow rate.

The flow rate adjustment module 310 can control the valves, pumps, or related accessories of the liquid chromatography system 200 and/or the delivery system 202 to establish a proper flow rate of a mobile phase through the microfluidic column device 100 by seamlessly applying a generated flow rate adjustment factor to an established flow rate prior to performing a sample analysis at the chromatography system 200 using the microfluidic column device 100 calibrated with respect to the reference column. For example, when an operator selects a desirable nominal flow rate, the corrected flow rate is seamlessly applied to the analysis.

Figure 4:
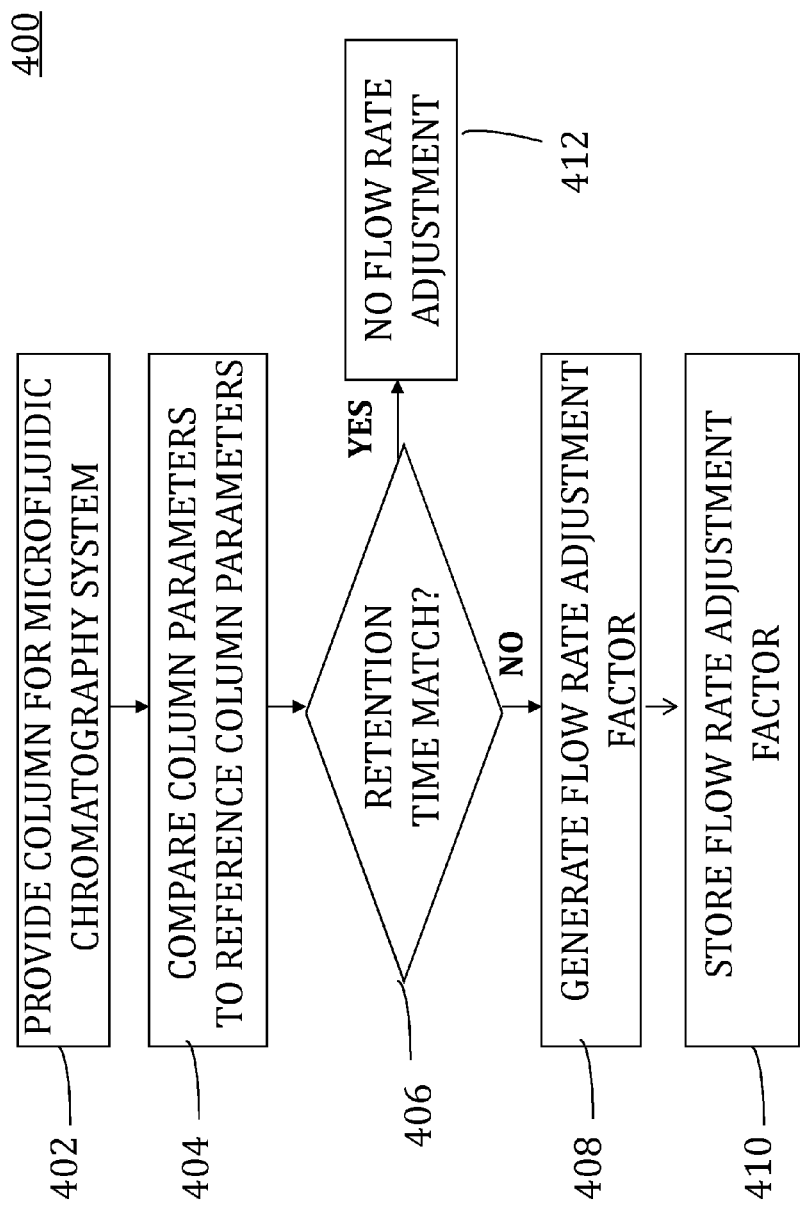
FIG. 4 is a flowchart illustrating a method for compensating for chromatography column volume variations, in accordance with an embodiment.

FIG. 4 is a flowchart illustrating a method 400 for compensating for chromatography column volume variations, in accordance with an embodiment. In describing the method 400, reference can be made to elements of FIGS. 1-3. In one embodiment, some or all of the method 400 is performed in concert with a microfluidic column operating in an isocratic elution mode. In another embodiment, some or all of the method 400 is performed in concert with a microfluidic column operating in a gradient elution mode.

At block 402, a column device 100 is provided for the microfluidic chromatography system 200 for performing a sample analysis or the like.

At block 404, at least one column parameter is compared to a corresponding reference column parameter. Column parameters can include, but not be limited to, a column volume, inner diameter, width, length, height, flow rate, retention time, related data, or a combination thereof. Certain column parameters are known at the time of implementation, for example, column dimensions such as a length, inner diameter, and so on.

A column comparison is made as part of a calibration of the column device 100. In one embodiment, the volume of the reference column is predetermined, for example, at a factory during quality control testing of the column. In other embodiments, no comparison is made; instead, an expected volume is calculated. A column volume can be determined from measured column dimensions, such as length (l), width (w), and/or thickness or depth (d) (see FIG. 1A). The volume can be determined when the reference column is empty, or when it is packed with a sorbent, preferably a same sorbent. The column device 100 and the reference column can include an unretained marker or a retained marker.

At decision diamond 406, during calibration, a determination is made from a parameter comparison, or expected volume calculation, whether a retention time is longer or shorter than an expected retention time, for example, the retention time of the reference column. In an embodiment, a retention time of a sample mixture in the microfluidic column 100 is measured in an isocratic elution mode. If the retention time at the column is different from a corresponding retention time of a sample mixture in the reference column, then the method 400 proceeds to block 408, where a flow rate adjustment factor (a) is generated, and used to adjust a flow rate of one or more samples in the column 100, for example, in accordance with Eq. (2A)-(5). Otherwise, the method 400 proceeds to block 412, where no flow rate adjustment is performed.

The flow rate adjustment factor (a) when applied to the actual flow rate can address and resolve the conventional problems related to retention time, for example, where it is difficult to identify peaks with accuracy due to varying results caused by different column volumes, and/or address and resolve problems related to separation selectivity when in a gradient mode.

Assuming that the sorbent packing density in the column is constant regardless of changes in column dimensions, the elution time of an unretained component, or the retained component if the retention factor is known, reflects the column volume, for example, described with reference to Eqs. 2A-2C above. A calibration can occur using an unretained marker, or a retained marker under isocratic conditions. In another embodiment, the volume of an empty column is measured, i.e. absent sorbent (see, for example, Eq. 2C above). In an embodiment, elution of the generated peaks is considered depending on the system volume, such as tubing, detectors, and so on. By applying known values with respect to the volume (V) and/or the measured retention time (t), the flow rate adjustment factor (a) can be determined (see, for example, Eqs. 3, 4).

At block 410, the flow rate adjustment factor can be stored, for example, in a storage device such as a memory 113 at the column device 100, or other memory location external from the column device 100. The flow rate adjustment factor can be applied to subsequent analysis provided to the column device 100, with no need for additional calibration of the column device 100. For example, when an operator selects a desirable nominal flow rate, the corrected flow rate is seamlessly applied to the analysis. The foregoing calibration steps can be performed for a new column device, whereby a new flow rate adjustment factor can be determined that compensates for volume variabilities with respect to the new column device. Accordingly, calibration can be performed for each new device, and a different flow rate adjustment factor can be applied for each device or column operation.

Figure 5:
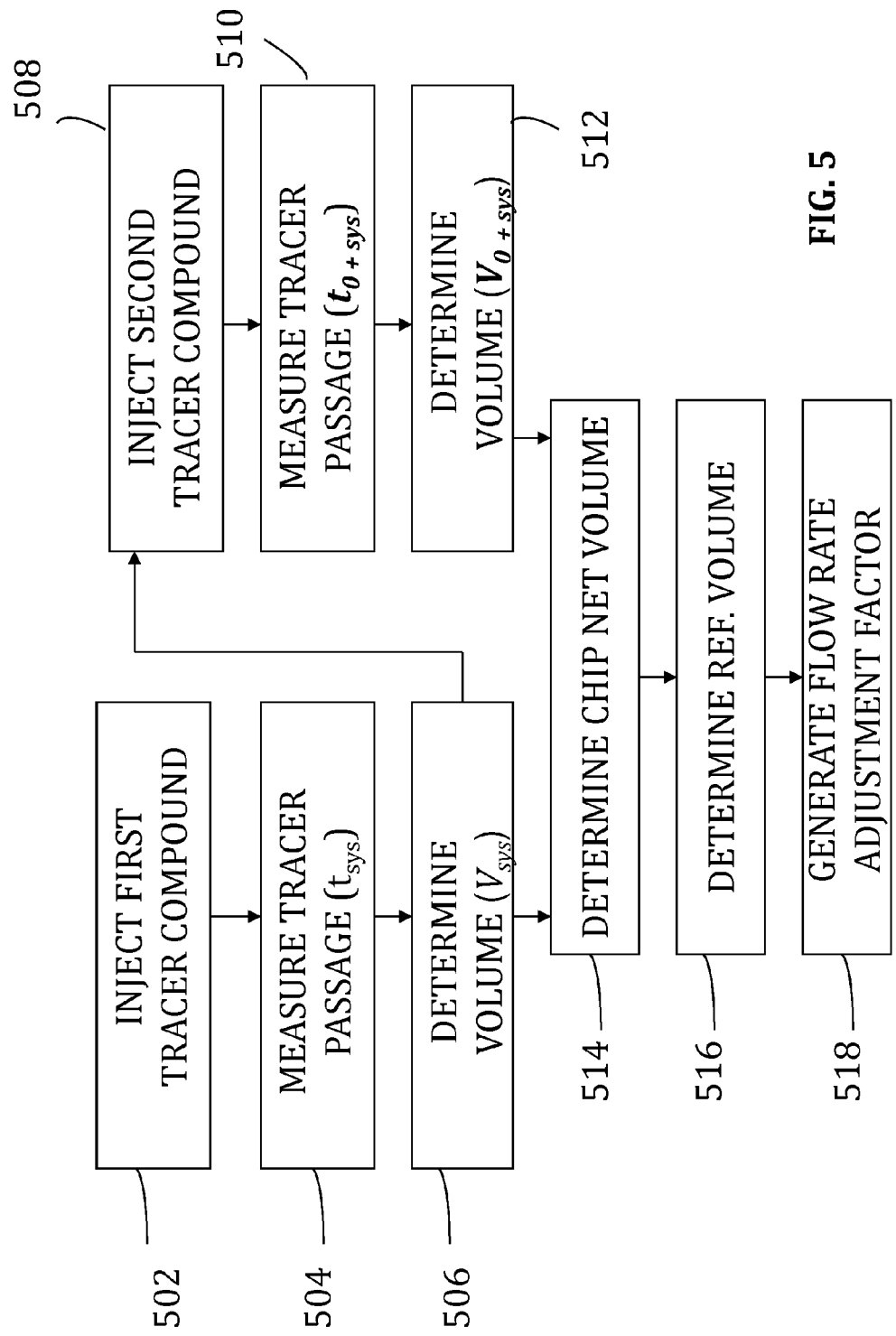
FIG. 5 is a flowchart illustrating a method for compensating for chromatography column volume variations, in accordance with another embodiment.

FIG. 5 is a flowchart illustrating a method 500 for compensating for chromatography column volume variations, in accordance with another embodiment. In describing the method 500, reference can be made to elements of FIGS. 1-3. In one embodiment, some or all of the method 500 is performed in concert with a microfluidic column operating in an isocratic elution mode. In another embodiment, some or all of the method 500 is performed in concert with a microfluidic column operating in a gradient elution mode.

At block 502, a first tracer compound is injected into a system, for example, an injector, for determining a system volume or other measurement in accordance with techniques known to those of ordinary skill in the art. At block 502, the system is absent a column or related microfluidic chip.

At block 504, a tracer passage time is measured. A system retention time ($t_{sys}$) can be determined from the measured tracer passage time.

At block 506, a system volume ($V_{sys}$) can be calculated according to the following equation:

$$V_{sys} = FR * t_{sys}, \qquad (Eq. 6)$$

where FR is a column flow rate, for example, similar to a flow rate described herein.

The method 500 proceeds to block 508, where a second tracer compound is injected. The second tracer compound can be the same as or similar to the first tracer compound. Here, the system includes a column that can be part of a microfluidic chip or related substrate element, which may otherwise include flow volumes or the like for measurement.

At block 510, a tracer passage time of the system including the chip is measured. Since the chip can include other flow passages such as vias and so on, the tracer passage time of the chip can be different from the tracer passage time determined at block 506. A retention time ($t_{0+sys}$) can be determined from the measured tracer passage time. At block 512, a volume ($V_{0+sys}$) can be calculated according to equation (Eq. 7):

$$V_{0+sys} = FR * t_{0+sys}, \qquad (Eq. 7)$$

where FR is a column flow rate, for example, similar to a flow rate described herein.

At block 514, a net volume of the chip can be determined, for example, according to the following equation:

$$V = V_{0+sys} - V_{sys} \qquad (Eq. 8)$$

At block 516, a reference volume ($V_{REF}$) is determined, for example, measured, calculated, or estimated according to an embodiment similar to or the same as other embodiments described herein.

At block 518, a flow rate adjustment factor (a) is generated, for example, according to the following equation:

$$a = V/V_{REF}, \qquad (Eq. 9)$$

where V is the net volume determined at Eq. 8, and wherein $V_{REF}$ is the reference column volume established at block 516. The flow rate adjustment factor (a) can be applied to adjust a flow rate, for example, described herein.

FIGS. 6(a)-6(c) are graphs illustrating the effects of column inner diameter variations on isocratic mode results. In particular, FIG. 6(b) illustrates a retention time of a mobile phase at a column having an inner diameter of 300 μm. FIG. 6(a) illustrates the retention time of a mobile phase at a column having an inner diameter that is slightly less than that of the column of FIG. 6(b), i.e., 290 μm. The retention time is shorter at FIG. 6(a) than at FIG. 6(b). FIG. 6(c) illustrates the retention time of a mobile phase at a column having an inner diameter that is slightly greater than that of the column of FIG. 6(b), i.e., 310 μm. The retention time is longer at FIG. 6(c) than at FIG. 6(b).

FIGS. 6(d)-6(f) are graphs illustrating the effects of column inner diameter variations on gradient mode results. In particular, FIG. 6(e) illustrates a retention time of a mobile phase at a column having an inner diameter of 300 μm. FIG. 6(d) illustrates the retention time of a mobile phase at a column having an inner diameter that is slightly less than that of the column of FIG. 6(b), i.e., 290 μm. The retention time is shorter at FIG. 6(d) than at FIG. 6(e). FIG. 6(f) illustrates the retention time of a mobile phase at a column having an inner diameter that is slightly greater than that of the column of FIG. 6(e), i.e., 310 μm. The retention time is longer at FIG. 6(f) than at FIG. 6(e). Also, as shown in FIGS. 6(d)-(f), in a gradient mode, the illustrated peaks can change relative retention. As their relative elution order changes, the resolution of the peaks can be affected, which can represent a problem in method transfer in a chromatography operation, for example, between chips.

The graphs shown in FIGS. 7(a)-7(c) are the same as those shown in FIGS. 6(d)-6(f), respectively. Accordingly, FIG. 7(a) illustrates a retention time of a mobile phase at a column having an inner diameter of 290 μm. FIG. 7(b) illustrates a retention time of a mobile phase at a column having an inner diameter of 300 μm. FIG. 7(c) illustrates a retention time of a mobile phase at a column having an inner diameter of 310 μm.

FIGS. 7(d)-7(f) are graphs illustrating the results of compensating for column inner diameter variations, in accordance with an embodiment. As shown in FIGS. 7(d)-7(f), the retention times are similar in each graph due to the application of a flow rate adjustment factor (a) generated in accordance with an embodiment. A determined column volume (V) can be calculated as a square of the measured inner diameter, for example, an inner diameter of 290 μm as shown in FIG. 7(d). In FIGS. 7(a)-7(f), the reference column is cylindrical. Accordingly, the reference column volume can be calculated as a square of the measured reference inner diameter of 300 μm. Accordingly, in FIGS. 7(d)-7(f), a flow rate adjustment factor (a) can be calculated by determining a ratio of a determined column volume or related measurement to a reference column volume or related measurement, for example, shown in the following equation:

$$a = d^2/d_{REF}^2 \quad \text{(Eq. 10)}$$

Alternatively, a column in accordance with other embodiments can have a square, rectangular, polygonal, or other dimensions requiring different well-known formulas to be applied for determining an area, volume, or the like. Accordingly, as shown in FIGS. 7(a)-7(f), reproducible column performance can be provided regardless of column-to-column volume variability.

As will be appreciated by one skilled in the art, aspects of the present inventive concepts may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

While the inventive concepts has been shown and described with reference to specific embodiments, it should be understood by those skilled in the art that various changes in form and detail may be made therein without departing from the spirit and scope of the inventive concepts.

What is claimed is:

1. A method of adapting to volume variations in microfluidic chromatography columns, the method comprising:
    calibrating a column by:
        comparing a parameter of the column with a same parameter of a reference column; and
        generating, by a processor, an adjustment factor in response to the comparison between the parameter of the column and the same parameter of the reference column; and
    compensating for volume differences between the calibrated column and the reference column by integrating the generated adjustment factor into a sample separation involving the calibrated column, wherein compensating for volume differences between the calibrated column and the reference column includes applying the adjustment factor to a flow rate during the sample separation.

2. The method of claim 1, wherein the adjustment factor is a ratio of a volume of the column and a volume of the reference column.

3. The method of claim 1, wherein the adjustment factor is a ratio of a retention time of the column and a retention time of the reference column.

4. The method of claim 1, further comprising:
    calibrating one or more other columns, wherein a different adjustment factor is generated for each of the other columns in response to a comparison between a parameter of each of the other columns and a same parameter of the reference column; and
    compensating for volume differences between the other calibrated columns and the reference column by integrating the different adjustment factors into sample separations involving the other calibrated columns.

5. The method of claim 1, wherein the column being calibrated is a microfluidic chromatography column.

6. The method of claim 1, wherein the column being calibrated has a rectangular, tubular, elliptical, polygonal, or semi-elliptical cross-sectional profile.

7. The method of claim 1, wherein the parameter of the column being calibrated includes at least one of a column volume and a retention time.

8. The method of claim 1, wherein the column being calibrated is constructed and arranged for a gradient elution.

9. The method of claim 1, wherein the column being calibrated is constructed and arranged for an isocratic elution.

10. The method of claim 1, further comprising:
    determining the parameter of the reference column by performing a physical measurement of a physical reference column or a calculated estimate of a reference value corresponding to a virtual reference column.

11. A column volume compensation system, comprising:
    a column volume comparator that compares a parameter of a column with a same parameter of a reference column;
    an adjustment factor processor that generates an adjustment factor in response to the comparison between the parameter of the column and the same parameter of the reference column; and
    an adjustment module that compensates for volume differences between the column and the reference column by integrating the generated adjustment factor into a sample separation involving the column, wherein the adjustment module includes the adjustment factor in a flow rate calculation during the sample separation.

12. The system of claim 11, wherein the adjustment factor processor generates the adjustment factor according to a ratio of a volume of the column and a volume of the reference column.

13. The system of claim 11, wherein the adjustment factor processor generates the adjustment factor according to a ratio of a retention time of the column and a retention time of the reference column.

14. The system of claim 11, further comprising a memory for storing the adjustment factor for application to a desirable nominal flow rate.

15. A method for compensating for volume variations in a microfluidic chromatography device, comprising:
   comparing a parameter of the column and the same parameter of a reference column
   generating, by a processor, an adjustment factor in response to the comparison between the parameter of the column with a same parameter of the reference column;
   performing a sample separation with the column; and
   adjusting a flow rate of the sample separation according to the adjustment factor.

16. The method of claim 15, wherein the adjustment factor is generated according to a ratio of a volume of the reference column and a volume of the column.

17. The method of claim 15, wherein the adjustment factor is generated according to a ratio of a retention time of the reference column and a retention time of the column.

* * * * *